(12) United States Patent
Beßler et al.

(10) Patent No.: US 12,239,770 B2
(45) Date of Patent: Mar. 4, 2025

(54) APPARATUS AND METHOD FOR PREPARING A MEDICAL SOLUTION

(71) Applicant: Vivonic GmbH, Sailauf (DE)

(72) Inventors: Patrick Beßler, Erlenbach (DE); Stefan Eberlein, Höchberg (DE); Andreas Hemm, Alzenau (DE)

(73) Assignee: VIVONIC GMBH, Sailauf (DE)

( * ) Notice: Subject to any disclaimer, the term of this patent is extended or adjusted under 35 U.S.C. 154(b) by 333 days.

(21) Appl. No.: 16/765,918

(22) PCT Filed: Nov. 20, 2018

(86) PCT No.: PCT/EP2018/081979
§ 371 (c)(1),
(2) Date: May 21, 2020

(87) PCT Pub. No.: WO2019/101757
PCT Pub. Date: May 31, 2019

(65) Prior Publication Data
US 2020/0360587 A1    Nov. 19, 2020

(30) Foreign Application Priority Data
Nov. 22, 2017   (DE) ...................... 10 2017 127 637.8

(51) Int. Cl.
*A61M 1/16*    (2006.01)
(52) U.S. Cl.
CPC ... *A61M 1/1666* (2014.02); *A61M 2205/7545* (2013.01)
(58) Field of Classification Search
CPC .............. A61M 1/1656; A61M 1/1666; A61M 2205/7545
See application file for complete search history.

(56) References Cited

U.S. PATENT DOCUMENTS

| 3,563,381 | A | * | 2/1971 | Edelson | .............. | A61M 1/1605 |
| | | | | | | 604/83 |
| 2002/0012619 | A1 | * | 1/2002 | Sano | ...................... | B01F 23/59 |
| | | | | | | 422/292 |
| 2013/0235691 | A1 | * | 9/2013 | Volker | ................ | A61M 1/1668 |
| | | | | | | 366/132 |

FOREIGN PATENT DOCUMENTS

| CN | 101374581 | 2/2009 |
| DE | 102012004886 | 9/2013 |

(Continued)

*Primary Examiner* — Dirk R Bass
(74) *Attorney, Agent, or Firm* — Kilyk & Bowersox, P.L.L.C.

(57) ABSTRACT

The present invention relates to an apparatus for preparing a medical solution and preferably a dialysis concentrate solution that has a fluid system having a main circuit and a branch section in communication therewith, wherein the main circuit is a circuit in which a pump and a product container are arranged and in which liquid can be circulated by operating the pump; and wherein a raw material container can be connected in the branch section; wherein the branch section comprises a suction line that leads from the raw material container to be connected to a suction unit of the main circuit; wherein the suction unit is configured to suck in liquid together with raw material not yet dissolved from the suction line and to introduce it into a liquid flowing through the main circuit; and wherein a fine mixing chamber that has two connectors and one retention element arranged between the connectors for undissolved raw material is furthermore arranged between the suction unit and the product container.

18 Claims, 4 Drawing Sheets

(56) References Cited

FOREIGN PATENT DOCUMENTS

Figure 1:
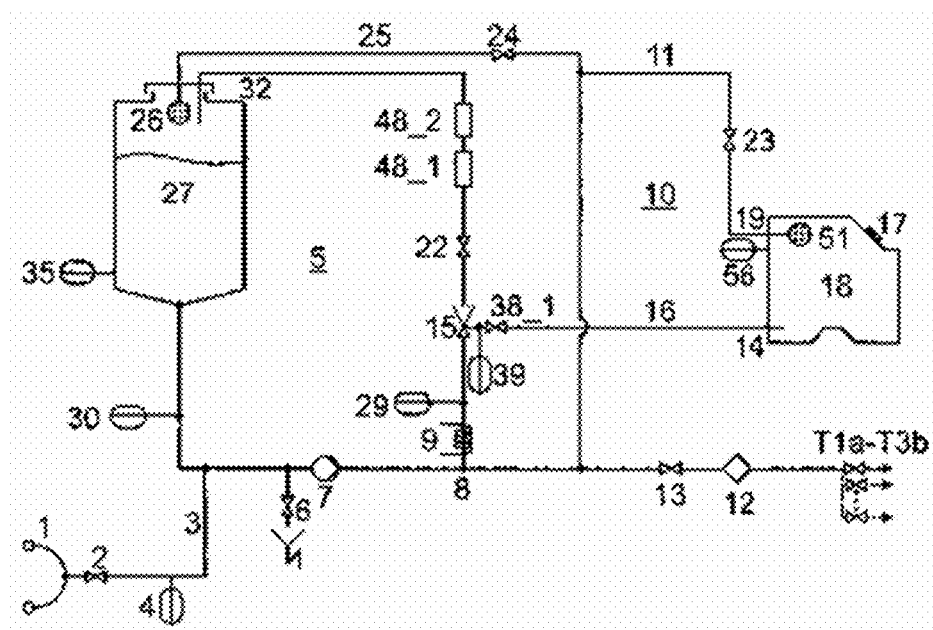

| | | |
|---|---|---|
| EP | 0491981 | 7/1992 |
| EP | 3100749 | 12/2016 |
| GB | 2097285 | 11/1982 |
| WO | 2011/000347 | 1/2011 |
| WO | 2016/066699 | 5/2016 |

\* cited by examiner

APPARATUS AND METHOD FOR PREPARING A MEDICAL SOLUTION

The invention relates to an apparatus and to a method for preparing a medical solution and preferably a dialysis concentrate solution.

A plurality of methods are known in the prior art for preparing dialysis concentrate solutions from non-dissolved or only partly dissolved raw materials. It is, for example, known to dissolve raw materials in a solvent, typically in RI water, which is also called a permeate or dialysis water, in a preparation tank with the aid of a stirrer. A cyclic sluicing in of water and sucking out of solvent directly into and out of a raw material container via a single connector are furthermore known. However, this process takes a relatively long time and the degree of dissolution is difficult to monitor.

It is furthermore known to have a raw material container flowed through by a solvent. The raw material container can, for example, have two connectors and can be flowed through from top to bottom or vice versa. Liquid is here typically continuously sluiced into the raw material container from above or from below and is sucked off at the bottom or top. However, some of the raw material moves into the product container in such a method if it is not prevented by separate measures. If non-dissolved raw material enters into the product container, there is a risk that it remains undissolved and the composition of the finished solution is not correct, i.e. does not meet the specifications. In these known methods, the raw material container additionally has to be designed as a pressure container since the build-up of excess pressure in the raw material container cannot be prevented.

It is the object of the invention to provide an apparatus and a method for preparing a medical solution and preferably a dialysis concentrate solution that makes it possible to mix raw materials of different consistencies accommodated in any raw material containers with a solvent with a high mixing security.

This object is achieved in accordance with the invention by an apparatus for preparing a medical solution and preferably a dialysis concentrate solution that has a fluid system having a main circuit and a branch section in communication therewith, wherein the main circuit is a circuit in which a pump and a product container are arranged and in which liquid can circulate by operating the pump, wherein a raw material container can be connected in the branch section, wherein the branch section comprises a suction line that leads from the raw material container to be connected to a suction unit of the main circuit, and wherein the suction unit is configured to suck in liquid together with raw material not yet dissolved from the suction line and to introduce it into a liquid flowing through the main circuit, wherein a fine mixing chamber that has two connectors and one retention element arranged between the connectors for undissolved raw material is furthermore arranged between the suction unit and the product container.

The apparatus is particularly suitable for preparing dialysis concentrate solutions, but is generally also suitable for preparing other medical solutions in which specific quantities of raw materials should be dissolved in a specific amount of a solvent or should be mixed therewith. The prepared solution can already be a solution ready to use or can be a concentrate such as a dialysis concentrate that has to be diluted again in a further step to obtain a ready-to-use solution.

When solvent or resulting solution is circulated in the main circuit of the fluid system by the operation of the pump, the liquid runs through the product container and the suction unit in so doing. The suction unit is preferably arranged between the pressure side of the pump and the product container in the main circuit. A lower pressure is present in the suction line in the operation of the apparatus than in the region of the main circuit comprising the suction unit due to the configuration of the suction unit such that liquid together with undissolved raw material is drawn out of the raw material container to be connected through the suction line into the main circuit. The raw material container connected using the suction line therefore does not have to be configured as a pressure container, but bags or the like can rather also be used as the raw material container. The raw material furthermore does not have to be configured as pressure-tight with respect to the environment even on an embodiment with a rigid wall, but can rather have openings for venting that are optionally closable.

Provision is made in an embodiment that the retention element comprises a filter element that holds back the still not dissolved raw material. The filter element here can be arranged such that the liquid with the raw material not yet dissolved has to flow against gravity to pass through the filter element. In addition, the fine mixing chamber can comprise a swirl chamber that the liquid reaches first before reaching the filter element and that extends about the filter element so that the liquid can support the dissolution of the not yet dissolved raw material due to the overflow that arises.

The fine mixing chamber is preferably arranged in the main circuit such that it is flowed through from bottom to top. Due to the arrangement of the fine mixing chamber in the direction of flow between the suction unit and the product container, raw materials do not move from the raw material container via the suction line into the product container without passing through the fine mixing chamber. A reliable intermixing is thus ensured and an entry of undissolved raw material into the product container is avoided.

Provision is made in an embodiment that at least two such fine mixing chamber are provided which are connected in series or in parallel and whose retention elements have different characteristics and preferably have particle permeabilities. Provision can, for example, be made that the retention capability of the fine mixing chamber disposed downstream in the direction of flow is finer than the retention capability of the fine mixing chamber disposed upstream in the direction of flow. This arrangement provides an ideal dissolution and avoids any clogging of the circuit. Generally, a combination of a plurality of fine mixing chambers connected in parallel and/or in series having identical or different retention capabilities is possible to optimize the intermixing.

Provision is made in an embodiment that the main circuit and the branch section are configured such that a raw material container to be connected can first be filled with liquid against the suction direction via the suction line and the suction unit before mixing operation starts. This process can also be repeated as required, e.g. controlled by time, filling quantities, or pressure. It thereby becomes possible to use solid or gelatinous raw materials that cannot be sucked in as such. The liquid introduced into the raw material container serves as a carrier liquid in which, for example, solid raw materials can be dispersed. The liquid containing raw material is then transported off through the suction line.

Provision is made in an embodiment that the suction unit is a Venturi valve, with the suction line opening into a narrowing section of the line of the main circuit. In this embodiment, liquid together with not yet dissolved raw material can be sucked out of the suction line and thus out of the connected raw material container by Venturi injection into the liquid circulating in the main circuit and can be taken along by it. The raw material container can be filled through the suction line against the suction direction by the Venturi nozzle by a pressure build-up with the aid of a closed regulation valve in the main circuit before mixing operation.

Provision is made in an embodiment that the branch section further has a flushing line that branches off from the main circuit between the pressure side of the pump and the suction unit and can be connected to the raw material container. In this embodiment, the branch section forms a closed bypass to the main circuit that leads over the connected raw material container. It can thus be achieved that solvent or produced dialysis concentrate solution from the main circuit can be mixed into the connected raw material container to flush through it. The flushing line can, however, in particular be used for cleaning the raw material container after use.

The raw material container can, for example, be a reusable container that can, but does not have to be formed as a pressure container. The latter can be filled through a fill connector with any raw material as the starting material for the solution to be prepared or for the dialysis solution concentrate. The raw material can be present in solid form, e.g. as a powder or as a granulate, as a solid/liquid mixture, or as a slurry, with it comprising at least partly undissolved components. Alternatively, the raw material container can be a film bag.

The apparatus in accordance with the invention is simultaneously suitable to be used with raw material containers that only have liquid components. A special adaptation of the apparatus is not necessary for such a case.

There is the option in an embodiment to short circuit the flushing line and the suction line to a coupling point so that the line can be flushed after decoupling the raw material container, for example to introduce any concentrate residues still into the main circuit or for cleaning purposes after ending the solution preparation.

Provision is made in an embodiment that at least one further branch section is present to which a further raw material container can be connected and which comprises a further suction line which leads from the further connected raw material container to a suction unit of the main circuit. The further suction line is preferably arranged in parallel with the first suction line and opens into the same suction unit of the main circuit. A plurality of suction units can, however, also be provided in the main circuit. It is possible in this embodiment to connect a plurality of raw material containers to the system that include different raw materials in different states of aggregation, for example. If a plurality of branch sections are provided, they can be identical or different. The above statements on preferred embodiments of the first branch section apply accordingly to every further branch section.

Provision is made in an embodiment that the fluid system has a supply line that opens into the main circuit. The fluid system can, for example, be connected to an RO water source via the supply line. The supply line preferably opens into the main circuit between the product container and the suction side of the pump.

Provision is made in an embodiment that the fluid system has a product line that branches off from the main circuit. Dialysis machines or solution containers, e.g. for storage, can, for example, be connected to the apparatus via the product line. The product line preferably branches off from the main circuit between the pressure side of the pump and the suction unit. The product line can also branch off from the flushing line of the branch section.

Provision is made in a further embodiment that the fluid system has a heating to heat liquid or solution located therein. The heating is preferably arranged in the main circuit and can be disposed, for example, between the pressure side of the pump and the suction unit.

The fluid system preferably comprises a plurality of valves with which the throughflow through the different lines of the system can be controlled. Regulation valves can, for example, be arranged in the main circuit between the suction unit and the product container and/or in the flushing line. A regulation valve can preferably be provided close to the suction unit in the suction line. Regulation valves can be arranged in the supply line and/or in the product line.

The initially stated object is also achieved by systems comprising an apparatus in accordance with the invention for preparing a medical solution, preferably a dialysis concentrate solution, and one or—if provided—more connected raw material containers.

Against the initially named background, the invention further relates to a method for manufacturing a medical solution and preferably a dialysis concentrate solution using an apparatus in accordance with the invention, wherein solvent or produced solution is circulated in the main circuit by operating the pump and raw materials are simultaneously sucked out of the suction line by the suction unit and are introduced into the liquid circulating in the main circuit. The sucked in raw materials are liquid raw materials or raw materials dissolved or dispersed in a carrier liquid.

Provision is made in an embodiment that solvent or produced solution from the main circuit is introduced into the raw material container via the dilution line, is mixed with the raw materials, and is drawn through the suction line together with the raw materials. Solvent or produced solution from the main circuit is therefore used as a carrier liquid for the raw material. This can be done once at the start of the preparation method or also multiple times or continuously during the preparation method.

The method can in particular be carried out automatically or partly automatically by a control unit that is present in mixing apparatus and that is configured to control the required actuators such as the pumps and valves and to read in measured values required therefor from sensors.

Against the initially named background, the invention further relates to the use of an apparatus in accordance with the invention for preparing a medical solution and preferably a dialysis concentrate solution.

Advantages of the invention include the option of an at least partly automatic mixing process for the complete dissolution of any raw materials. Due to the fine mixing chamber having a retention element for not yet dissolved raw materials, a complete dissolution of the raw material can be ensured. Raw material introductions into the product container are avoided. In some embodiments, the mixing process is self-regulating, as will be explained in the following. It is possible to connect any desired raw material bundles such as flexible disposable bags and rigid reusable containers as the raw material source. The consistency of the raw material can be selected as desired. A processing of solid raw materials is just as possible as a processing of gelatinous or liquid raw materials.

Figure 2:
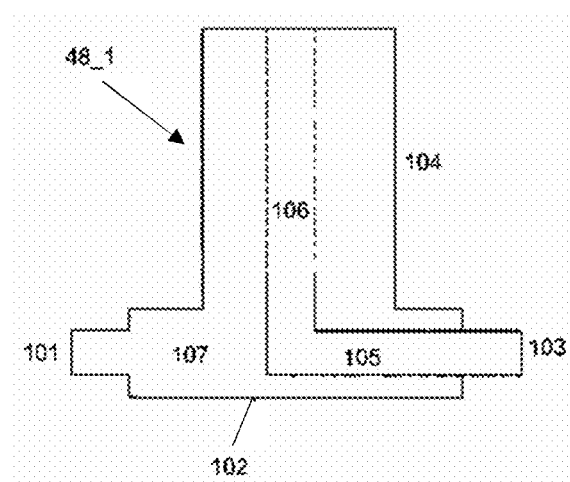
Figure 3:
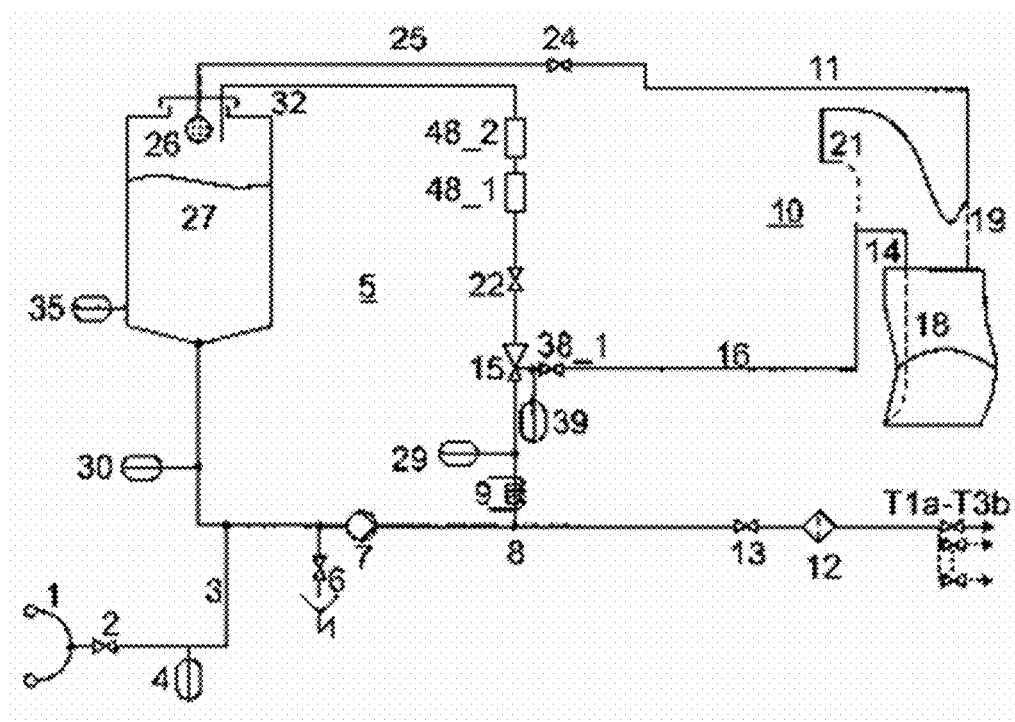
Figure 4:
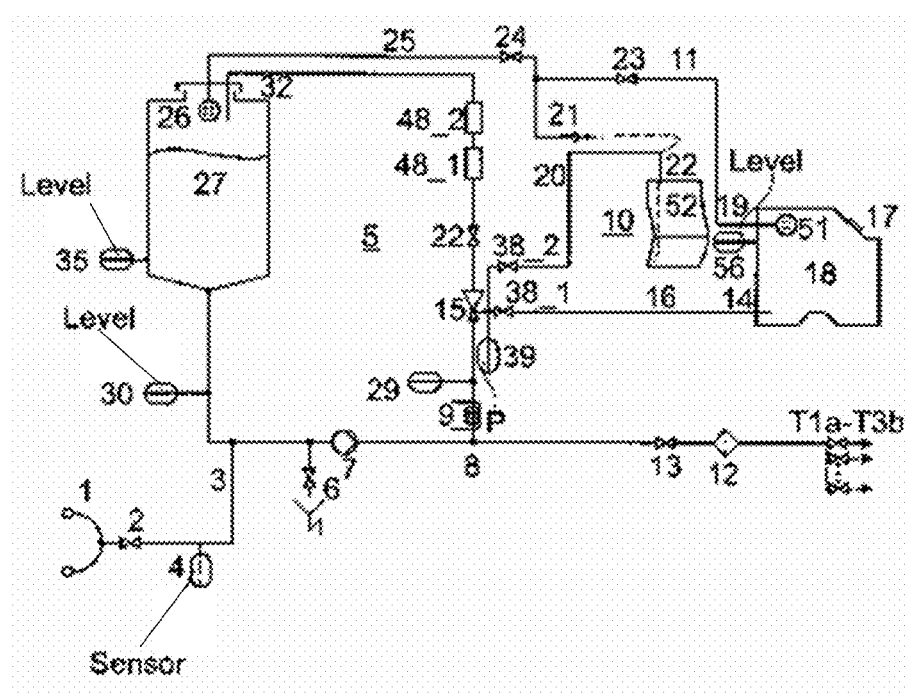

Further details and advantages of the invention result from the embodiments described in the following with reference to the Figures. There are shown in the Figures:

FIG. 1: a flow chart of an embodiment of a system of an apparatus in accordance with the invention for preparing a dialysis concentrate solution with a connected raw material container;

FIG. 2: a section through an embodiment of a fine mixing chamber with a retention element formed as a filter element;

FIG. 3: a flow chart of an embodiment of a further system of an apparatus in accordance with the invention for preparing a dialysis concentrate solution with a connected raw material container designed as a disposable bag; and FIG. 4: a flow chart of an embodiment of yet another system of an apparatus in accordance with the invention for preparing a dialysis concentrate solution with two connected raw material containers.

The embodiment shown in FIG. 1 of an apparatus in accordance with the invention comprises a supply connector 1 for solvent having a supply line 3 in which a supply valve 2 is arranged. The supply line 3 opens into a main circuit 5 in which inter alia a pump 7, a first regulation valve 22, and a product container 27 are arranged.

In a first preliminary step for preparing a dialysis concentrate solution, RO water is filled as a solvent through the supply line 3 into the product container 27 by the charging pressure applied at the supply connector 1 with an open valve 2. The quantity of the liquid that has run into the product container 27 or its filling level can be determined with reference to the flowmeter 4 or with reference to the filling level sensors 30 and 35. A gravimetric sensor, not shown in the Figure, can furthermore be provided to determine the filling level in the product container 27. After completion of this preliminary step, the supply valve 3 can be closed.

The apparatus further comprises a branch section 10 that is in communication with the main circuit 5. The branch section 10 branches off from the main circuit 5 at a branch point 8 at the pressure side of the pump 7 and comprises a flushing line 11, a second regulation valve 23, and a suction line 16 that comprises a further regulation valve 38_1. The suction line 16 and the flushing line 11 are connectable to a raw material container 18.

The suction line 16 opens into the main circuit 5 at a suction unit 15 configured as a Venturi nozzle. The raw material container 18 in the embodiment in accordance with FIG. 1 is a rigid container that can be reused multiple times and that has a connector 19 for the flushing line 11, a connector 14 for the suction line 16, and a filling connector 17 for filling and, optionally, emptying the raw material container 18. A filling level sensor 56 is furthermore provided for determining the filling level in the raw material container 18, in particular for avoiding an overflow of the raw material container 18.

In a second preliminary step for preparing a dialysis concentrate solution, the raw material container 18 is connected to the apparatus. If the raw material container is not already filled with raw material, it can be filled with a specific quantity of a raw material through the filling connector 17. It can here be a solid raw material, for example a powder or a granulate, or a high viscosity concentrate, for example a slurry or low viscosity concentrate. The (re)filling can take place in the connected state or in the disconnected state of the raw material container.

On a use of solid materials or high viscosity concentrates, provision can be made in a third preliminary step to pump some of the solvent from the product container 27 using the pump 7 on opening the valve 38_1 and with a closed regulation valve 22 through the suction line 16 against the suction direction into the raw material container 18 that is for this purpose vented to the environment by a venting means, not shown. This portion of the solvent serves as a transport medium for, for example, the solid raw material that is at least dispersed therein, albeit still hardly dissolved in this step, and is thus made line-capable.

The order of the preliminary steps can substantially be as desired with the only limitation that the product container 27 has to be filled with solvent before a portion of the solvent located therein is pumped into the raw material container 18. Provision can, for example, be made only to fill raw material into the raw material container 18 after a partial filling with solvent. The filling of the raw material container 18 with the raw material can also take place before the filling of the product container 27 with solvent.

At the start of the mixing process, solvent is circulated out of the product container 27 in the main circuit 5 using the pump 7 with an open first regulation valve 22. Liquid raw material or raw material dispersed and not dissolved in liquid is here sucked into the solvent circulating in the main circuit 5 from the connected raw material container 18 through the section line 16 at the suction unit 15 through injection and is taken along. In the direction of flow downstream of the suction unit 15, fine mixing chambers 48_1 and 48_2 arranged in series are provided in series in the main circuit 5. The not yet dissolved raw material is dissolved in solvent in the fine mixing chambers 48_1 and 48_2. The fine mixing chambers 48_1 and 48_2 each comprise a retention element provided for the undissolved components of the raw material. The presence of two fine mixing chambers 48_1 and 48_2 serves the optimization of the apparatus in accordance with the invention. The principle of the invention only requires the presence of at least one fine mixing chamber 48_1.

FIG. 2 shows an embodiment for such a fine mixing chamber 48_1 and 48_2 in which the retention element is configured as a filter element. The liquid having the at least partially undissolved raw concentrate material is flowed into the fine mixing chamber housing 104 laterally downwardly and preferably with a lateral offset through the inflow 101 of the fine mixing chamber and moves into a swirl chamber 107 that extends around the filter element 106. Alternatively, the fine mixing chamber can also be positioned at the bottom (102) instead of laterally at the fine mixing chamber housing 104.

A swirl arises in the swirl chamber 107 in the fine mixing chamber housing 104 by the flowing in of the suspension from laterally below or from below. To arrive at the filter element 106, the liquid having the not yet dissolved raw material has to flow through the swirl chamber 107 upwardly against gravity. Undissolved components are here preferably held in the swirl chamber 107 by the swirl and by gravity where their dissolution is accelerated by the swirl. Undissolved components nevertheless arriving at the filter element are retained at the filter element 106 and are dissolved by the overflowing of the liquid. The liquid or solution flowing through the filter element 106 is collected in the manifold 105 and is led via the outflow 103 of the fine mixing chamber 48_1 further into the mixing line of the mixing system either to a further fine mixing chamber 48_2 (as shown in FIG. 1) or directly back into the product container 27.

The filter element of the second fine mixing chamber 48_2 can have a finer particle permeability than the filter element of the first fine mixing chamber 48_1, i.e. the retention capability of the first fine mixing chamber can be less than that of the second fine mixing chamber 48_2 to promote a step-wise dissolution of the raw material.

The liquid exiting the fine mixing chambers 48_1 and 48_2 arrives back in the product container 27. The filters of the fine mixing chambers 48_1 and 48_2 allow liquid to pass in accordance with their retention capability and hold back any undissolved raw material particles to the required degree. It can thus be avoided that raw material particles arrive in the product container 27.

The solvent can be heated before and during the dissolution process to accelerate and optimize the dissolving process. For this purpose, a continuous-flow heater 9 and a temperature sensor 29 are arranged in the main circuit 5 upstream of the suction unit 15 and the fine mixing chambers 48_1 and 48_2 in the direction of flow.

A regulation valve 38_1 and a sensor 39, that can be configured as a pressure sensor, are arranged just before the opening into the suction unit 15 in the suction line 16. The sensor 39 serves the monitoring of the mixing process and the filling level recognition of a connected raw material container 18. The suction line 16 can be interrupted as required by the regulation valve 38_1, e.g. when the raw material container 18 is empty and a suction of air should be prevented.

The solvent or the produced dialysis concentrate solution is circulated for so long in the main circuit 5 until the total raw material is dissolved that is contained in the connected raw material container 18. It can be necessary in this process to carry out an interposed step a plurality of times in the course of the dissolution process, said step corresponding to the third preliminary step described above, that is to pump a portion of the solvent from the product container 27 through the suction line 16 of the branch section 10 into the connected raw material container 18 using the pump 7 with a suitable position of the regulation valves 22 and 38_1 to make further portions of the raw material, that is solid for example, line-capable. The complete consumption of the raw material can be monitored using a time control and/or using the sensor 39. A gravimetric sensor or an otherwise suitable sensor can furthermore be arranged at the raw material container 18.

Once the total raw material located in the raw material container 18 is consumed and the raw material container 18 has been sucked empty by the suction unit 15, the dissolution process and the circulation of the now ready dialysis concentrate solution in the main circuit 5 can be ended or circulation can be continued for a certain time beforehand so that residues of undissolved raw material remaining in the fine mixing chambers are also dissolved. The apparatus can optionally have sensors for the automatic quality control of the dialysis concentrate solution such as density sensors, conductivity measurement cells or refractometers.

The retention of undissolved raw material particles in a fine mixing chamber 48_1 and 48_2 respectively is a substantial advantage of the solution in accordance with the invention. In static mixers such as are frequently used in the prior art, the raw material is dissolved by swirling with the solvent and the mixture is then pumped into a product container. Undissolved raw material likewise enters into the product container. In the course of the preparation method in accordance with the invention or as part of the apparatus in accordance with the invention, no dissolution of raw material takes place in the product container 27 since the undissolved raw material does not enter into the product container 27 at all due to the fine mixing chamber.

If the retention element in the fine mixing chamber 48_1 and 48_2 is configured as a filter element, the system can operate in a self-regulating manner while including the suction unit 15 without any further auxiliary means. If undissolved raw material reduces the throughflow through the filter element, the flow through the suction unit that is configured as a Venturi nozzle in this embodiment is reduced. Less undissolved raw material is thereby sucked in and introduced into the fine mixing chamber until the clogging raw material portions release due to the overflowing liquid and reduce or even end the clogging again, whereby the throughflow increases again. This self-regulation promotes the dissolving of the raw material and simultaneously prevents a significant clogging of the retention element and thus of the liquid flow with the raw material.

The completed dialysis concentrate solution can be pumped to different consumer stations T1$a$-T3$b$ such as dialysis machines or solution containers, e.g. for storage, through a product line having a filter 12 and a transfer valve 13 using the pump 7.

On completion of the process, the system and all the flow paths can be flushed and optionally disinfected. For this purpose, cleansing liquid, for example RO water or RO water admixed with peroxides (that was e.g. metered into the container 27 from the supply connector 1 or admixed with peroxides) can be pumped through the lines of the system using the pump 7. The cleansing can include a connected raw material container 18 before it should again be filled with raw material at the same position or at a separate position or should be cleansed or disposed of. The apparatus can also be configured such that it prepares the liquid required for the cleaning itself as in the case of the medical solution with the aid of a raw material container 18 filled with a disinfecting agent or disinfecting solution.

A spray head 51 connected to the flushing line 11 is provided in the raw material container 18 for the purpose of the cleaning. A spray head 26 is also provided in the product container 27 and is connected to a cleansing line 25 with a cleansing valve 24. The cleansing line 25 branches off from the flushing line 11 of the branch section 10. A flushing of the raw material container 18 and of the product container 27 can therefore be carried out in that cleansing liquid arrives in the flushing line 11 and from there, depending on the position of the second regulation valve 23 and of the cleansing valve 24, into the spray head 51 of the raw material container 18 and/or into the spray head 26 of the product container 27 and is sprayed into the respective container by the pump 7 with an open supply valve 2 and a closed first regulation valve 22. It is also possible that the cleansing liquid is first metered into the container 27 via the supply connector 1 before the circulation by the pump 7. The main mixing paths can also be cleansed by opening the first regulation valve 22 and closing the regulation valves 23 and 24. If the flow relationships allow, the regulation valves 22, 23, and 24 can also simultaneously be open during the cleansing process. Consumed cleansing solution can be discarded through the outflow 6.

FIG. 3 shows a flow chart of a further embodiment of an apparatus in accordance with the invention for preparing a dialysis concentrate solution. The flow chart is generally similar to that of FIG. 1 and only differences will be discussed in the following.

In contrast to the apparatus of FIG. 1, no rigid container that is usable multiple times is used as the raw material container in the apparatus of FIG. 3, but a flexible disposable bag 18 is rather used.

The disposable bag 18 has an optional connector 19 for the line 11 that here optionally serves the venting and has a connector 14 for the suction line 16 of the branch section 10. The connection between the optional connector 19 and the line 11, on the one hand, and the connector 14 and the suction line 16, on the other hand, is releasable. The corresponding connectors can, for example, be equipped with fast-closing couplings. A coupling point 21 is located close to the connector point of the disposable bag 18 at the machine side and both the end of the line 11 connectable to the optional connector 19 and the end of the section line 16 connectable to the connector 14 can be connected thereto. The coupling point 21 has a line portion having two connectors, for example fast-closing couplings.

The end of the line 11 is connected to the coupling point 21 or, in the case of an optional connector 19, selectively to the connector 19. The end of the suction line 16 can selectively be connected to the connector 14 or to the coupling point 21. If both ends are connected to the coupling point, a closed circuit is formed while omitting the bag 18. This configuration should be present during the cleansing of the system and generally always when no bag is connected. A connection of the end of the suction line 16 to the connector 14 replaces the second preliminary step described in connection with FIG. 1. This configuration is shown in FIG. 3.

A connection of the end of the line 11 to the connector 19 can be carried out in connection with the third preliminary step described with respect to FIG. 1 when a venting of the bag during a possible filling via the suction line 16 is desired. It can, however, also be the case, particularly with disposable bags, that the bag 18 is already sufficiently filled with liquid for flushing the undissolved raw materials at the manufacturer's side so that a filling process with liquid is dispensable or partially dispensable.

The medical solution and preferably the dialysis concentrate solution is subsequently mixed and prepared as already explained.

In the case of this embodiment, the dissolution process can be ended once the total liquid containing raw material located in the bag 18 has been sucked empty and residual raw material quantities remaining in the fine mixing chambers have been dissolved.

The bag 18 is separated and the suction line 16 and the line 11 are—if not already connected—short-circuited via the coupling point 21 for the subsequent cleansing. To cleanse the suction line 16 and the lines 11 and 25, the regulation valves 38_1 and 24 have to be open.

An apparatus in accordance with the invention can naturally be designed such that both a rigid raw material container usable multiple times as in FIG. 1 and a flexible disposable bag as in FIG. 3 can be connected. Alternative connectors and/or slots can be provided for this purpose.

FIG. 4 shows a flow chart of yet another embodiment of an apparatus in accordance with the invention. The flow chart substantially corresponds to a combination of the embodiments shown in FIGS. 1 and 3.

In the apparatus of FIG. 4, a second suction line 20 having a second regulation valve 38_2 is provided that extends in parallel with the first suction line 16 and opens into the first suction line 16 at the measurement point of the sensor 39 between the regulation valve 38_1 and the suction unit 15, that is just before the suction unit 15. This second suction line 20 serves the connection of a second raw material container 52 in the form of a disposable bag filled with a liquid. A liquid concentrate or an active ingredient solution can be present in this bag 52 and should be introduced into the dialysis concentrate solution in addition to the raw material of the raw material container 18. For this purpose, the end of the second suction line 20 is connectable to the connector 22 of the second raw material container 52. On a circulation of the solvent or of the produced dialysis concentrate solution in the main circuit 5 and on a flowing through of the suction unit 15, not only liquid containing raw material is sucked into the solvent circulating in the main circuit 5 and is taken along by Venturi injection through the suction line 16, but also an additional raw material through the second suction line 20 (for example alternately or simultaneously).

In the case of this embodiment, the dissolving process can be ended once the total liquid containing raw material located in the container 18 and the total additional content located in the bag 52 have been sucked empty and the residual raw material quantities remaining in the fine mixing chambers have been dissolved.

If no additional raw material container 52 is connected, for example on a non-use or on a flushing of the circuit, the end of the second suction line 20 can be connected to a coupling point 21 departing from the flushing line 11 and having a check valve, said coupling point comprising a suitable connector, for example a fast-closing coupling. In the case of the embodiment of FIG. 4, a venting option of the container 52 can furthermore be provided via a connection as in the case of the embodiment of FIG. 3, which is not shown in any more detail in FIG. 4.

The invention claimed is:

1. An apparatus for preparing a medical solution comprising a fluid system having a main circuit and a branch section in communication with the main circuit, the main circuit comprises a suction unit, a pump, a fine mixing chamber, and a product container, and the branch section comprises a suction line, wherein the main circuit is a circuit in which the pump and the product container are arranged and that is configured to circulate liquid by operating the pump, the branch section is configured to connect to a raw material container containing a raw material that is at least partly not dissolved, therein, the suction line is configured to be connected to the raw material container and is connected to the suction unit of the main circuit, the suction unit is configured to suck in liquid together with the raw material at least partly not dissolved, from the suction line, and to introduce the liquid with the raw material at least partly not dissolved into a liquid flowing through the main circuit, the fine mixing chamber comprises an inlet, an outlet, a swirl chamber, a manifold, and a retention element arranged between the inlet and the manifold, the retention element being configured to retain undissolved raw material, the fine mixing chamber is arranged between the suction unit and the product container, the swirl chamber extends around the retention element, liquid passing through the fine mixing chamber enters the inlet, flows into the swirl chamber, and flows upwardly and through the retention element and into the manifold before exiting through the outlet, during operation a swirl is created in the swirl chamber, and during operation, the raw material at least partly not dissolved is held in the swirl chamber, spaced apart from the retention element, by the swirl and by gravity.

2. The apparatus in accordance with claim 1, wherein the retention element is a filter element arranged such that the liquid having the raw material at least partly not dissolved has to flow against gravity to pass through the filter element.

3. The apparatus in accordance with claim 1, further comprising a second fine mixing chamber that is connected in series with or in parallel with the first mentioned fine mixing chamber, wherein
- the second fine mixing chamber is arranged between the suction unit and the product container,
- the second fine mixing chamber comprises an inlet, and outlet, a swirl chamber, a manifold, and a second retention element arranged between the inlet and the manifold,
- the second retention element is configured to retain undissolved raw material,
- the second fine mixing chamber comprises a second swirl chamber, and
- the retention element and the second retention element have different particle permeabilities relative to one another.

4. The apparatus in accordance with claim 1, wherein the suction unit is an active suction unit comprising a pump, or a passive suction unit.

5. The apparatus in accordance with claim 1, wherein the suction unit comprises a Venturi nozzle and the suction line opens into a narrowing portion of the main circuit.

6. The apparatus in accordance with claim 1, wherein the branch section further comprises a flushing line that branches off of the main circuit between a pressure side of the pump and the suction unit, and that is connectable to the raw material container.

7. The apparatus in accordance with claim 1, wherein the fluid system further comprises at least one further branch section to which a further raw material container is connectable, the at least one further branch section comprises a further suction line that leads from the further raw material container and is connected to the suction unit of the main circuit.

8. A system comprising an apparatus in accordance with claim 1 and a raw material container connected to the suction line.

9. A system comprising an apparatus in accordance with claim 7, a raw material container connected to the suction line, and at least one further raw material container connected to the further suction line.

10. A method for preparing a medical solution and preferably a dialysis concentrate solution using an apparatus in accordance with claim 1, comprising
- operating the pump to circulate a liquid comprising solvent or produced solution, in the main circuit, and
- simultaneously sucking raw materials out of the suction line through the suction unit and introducing the raw materials sucked out of the suction line into the liquid circulating in the main circuit.

11. The method in accordance with claim 10, further comprising
- introducing solvent or produced solution from the main circuit, via a dilution line, into the raw material container,
- mixing the solvent or produced solution introduced via the dilution line, with the raw materials in the raw material container, to form diluted raw materials, and drawing the diluted raw materials through the suction line.

12. The method in accordance with claim 10, wherein the preparation of the solution takes place in a self-regulating manner with the aid of the fine mixing chamber arranged in the main circuit and with the aid of the retention element included therein.

13. An apparatus for preparing a medical solution comprising a fluid system having a main circuit and a branch section in communication with the main circuit, the main circuit comprises a suction unit, a pump, a fine mixing chamber, and a product container, and the branch section comprises a suction line, wherein
- the main circuit is a circuit in which the pump and the product container are arranged and that is configured to circulate liquid by operating the pump,
- the branch section is configured to connect to a raw material container containing a raw material that is at least partly not dissolved, therein,
- the suction line is configured to be connected to the raw material container and is connected to the suction unit of the main circuit,
- the suction unit is configured to suck in liquid together with the raw material at least partly not dissolved, from the suction line, and to introduce the liquid with the raw material at least partly not dissolved into a liquid flowing through the main circuit,
- the fine mixing chamber comprises an inlet, an outlet, a swirl chamber, a manifold, and a retention element arranged between the inlet and the manifold, the retention element being configured to retain undissolved raw material,
- the fine mixing chamber is arranged between the suction unit and the product container,
- the swirl chamber extends around the retention element,
- the retention element and the manifold intersect at an overflow,
- the overflow has a first height during operation,
- the inlet of the fine mixing chamber has a second height during operation, and the second height is lower than the first height, and
- liquid passing through the fine mixing chamber flows upwardly before reaching the retention element, and flows through the retention element and over the overflow into the manifold before exiting through the outlet.

14. The apparatus in accordance with claim 13, wherein, during operation, the outlet of the fine mixing chamber has a height that is less than the first height of the overflow.

15. The apparatus in accordance with claim 13, wherein, during operation, the swirl chamber has a height that extends above the first height of the overflow.

16. The apparatus in accordance with claim 1, wherein the retention element is a filter.

17. The system of claim 8, further comprising a control unit configured to continuously run the system to prepare the medical solution.

18. The system of claim 8, further comprising a control unit configured to automatically run the system to prepare the medical solution.

* * * * *